(12) United States Patent
Gut

(10) Patent No.: US 9,164,116 B2
(45) Date of Patent: Oct. 20, 2015

(54) WASH ELEMENT, WASH STATION AND PROCESS FOR WASHING REUSABLE FLUID MANIPULATORS

(75) Inventor: Raphael Gut, Luzern (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 792 days.

(21) Appl. No.: 13/177,794

(22) Filed: Jul. 7, 2011

(65) Prior Publication Data

US 2012/0017945 A1  Jan. 26, 2012

(30) Foreign Application Priority Data

Jul. 21, 2010  (EP) ..................................... 10170249

(51) Int. Cl.
- B08B 3/00  (2006.01)
- G01N 35/10  (2006.01)
- B05B 1/26  (2006.01)
- B08B 3/02  (2006.01)
- B01L 9/00  (2006.01)

(52) U.S. Cl.
CPC ............ G01N 35/1004 (2013.01); B05B 1/267 (2013.01); B08B 3/02 (2013.01); B01L 9/52 (2013.01)

(58) Field of Classification Search
USPC ............... 345/1.1, 1.2, 11, 30, 33; 340/995.1, 340/995.11, 995.15, 995.24, 995.27
See application file for complete search history.

(56) References Cited

U.S. PATENT DOCUMENTS

| | | |
|---|---|---|
| 4,730,631 A | 3/1988 | Schwartz |
| 5,133,373 A | 7/1992 | Hoffman et al. |
| 5,813,087 A | 9/1998 | Huffman |
| 7,300,525 B2 | 11/2007 | Fuerst et al. |
| 2010/0135853 A1* | 6/2010 | Broga et al. .................... 422/51 |

FOREIGN PATENT DOCUMENTS

| | | |
|---|---|---|
| DE | 29614705 U1 | 2/1998 |
| EP | 1129793 A3 | 9/2001 |
| FR | 2652763 A1 | 4/1991 |
| JP | H06-258329 A | 9/1994 |

(Continued)

OTHER PUBLICATIONS

English translation of FR 2652763 to Auge et al., translated Oct. 2014.*

(Continued)

Primary Examiner — Eric Golightly
(74) Attorney, Agent, or Firm — Roche Diagnostics Operations, Inc.

(57) ABSTRACT

A wash element for washing one or more reusable fluid manipulators is provided comprising at least one nozzle for connection to a fluid pump to generate a fluid jet and at least one deflector surface positioned to deflect the fluid jet towards a washing zone for receiving at least a portion of the fluid manipulator. The deflector surface is being shaped to broaden the fluid jet. The invention further relates to a wash station having a cavity provided with one or more wash elements. The invention yet further relates to an automated system for manipulating fluids comprising at least one wash station and a controller set up to control washing the fluid manipulator. In a process for washing the reusable fluid manipulator at least a portion of the fluid manipulator is moved in a washing zone, a fluid jet of washing fluid is generated and directed onto a deflector surface shaped to broaden and deflect the fluid jet towards the washing zone.

10 Claims, 10 Drawing Sheets

(56) References Cited

FOREIGN PATENT DOCUMENTS

| JP | H06-296574 A | 10/1994 |
|---|---|---|
| JP | H09-292398 A | 11/1997 |
| JP | 2008-224245 A | 9/2008 |
| JP | 2008-246446 A | 10/2008 |
| JP | 2010-101726 A | 5/2010 |
| WO | 9912666 A1 | 3/1999 |

OTHER PUBLICATIONS

European Search Report dated Feb. 4, 2011 from Application No. 10170249.6-1234.

* cited by examiner

WASH ELEMENT, WASH STATION AND PROCESS FOR WASHING REUSABLE FLUID MANIPULATORS

TECHNICAL FIELD

The present invention relates generally to the automated processing of samples involving manipulation of fluids by reusable fluid manipulators such as pipettes and stirrers and, more particularly, to a wash element, a wash station and a process for washing the fluid manipulators. It further relates to a system for the automated manipulation of fluids by one or more reusable fluid manipulators provided with at least one wash station for washing the fluid manipulators.

BACKGROUND OF THE INVENTION

Various types of clinical analyzers for the automated analysis of samples such as blood, serum, urine and plasma are in practical use. Since there is a strong demand for offering a wide variety of analytical functions and with a view to improve effectiveness in sample processing, modern analyzers usually process samples in parallel and/or split individual samples into a number of aliquots for simultaneous processing. As a result, modern analyzers are subject to a number of pipetting operations. Otherwise, analysis typically requires the samples to be combined with one or more reagents by use of pipettes to initiate chemical or immunochemical reactions with respect to specific substances contained therein. Some reagents such as suspensions of magnetic beads need to be homogenized before use which most typically is done with stirrers having paddles on their free ends which are lowered into the reagents.

It has been found advantageous to employ reusable pipettes and stirrers which compared to disposables reduce the costs of sample processing. Thorough washing of the outside surfaces of such reusables is however required in-between consecutive operations to avoid carry-over and cross-contamination.

Washing devices for washing the outer surfaces of pipettes and stirrers are known from the prior art. It is common practice to insert these objects into a cavity filled with washing fluid which, however, does not always yield the desired result. The washing fluid has to be replaced after one or more washing steps resulting in a lot of waste fluid. A more sophisticated washing device is described in U.S. Pat. No. 7,300,525 B2. This washing device comprises a cavity for holding a washing fluid provided with a fluid duct for filling or emptying the cavity. Furthermore, one or more nozzles are directed towards the interior of the cavity to dispense washing fluid directly onto the pipettes. Another approach is described in U.S. Pat. No. 4,730,631, in which both the inside and outside surfaces of pipettes are washed by lowering the pipettes into a receptacle and forcibly dispensing washing fluid therethrough to fill the receptacle with washing fluid.

SUMMARY OF THE INVENTION

It is against the above background that the present invention provides certain unobvious advantages and advancements over the prior art. In particular, the inventors have recognized a need for improvements in wash elements, wash stations, and processes for washing reusable fluid manipulators.

Although the present invention is not limited to specific advantages or functionality, it is noted that the present invention addresses the problem of carry-over and cross-contamination in the automated analysis of samples. The invention provides improved equipment that can be used for washing fluid manipulators such as pipettes and stirrers effectively. The embodiments of the invention also enable effective washing of various kinds of fluid manipulators. The present invention further provides an equipment having a simple mechanical design that can readily be integrated into existing automated clinical analyzers for analyzing fluid samples.

In accordance with one embodiment of the invention, a wash station for washing one or more reusable fluid manipulators of an automated system for the automated manipulation of fluids is provided. The wash station comprises a cavity for inserting the one or more fluid manipulators. The cavity has one or more washing zones, each of which is sized to receive at least a portion of at least one fluid manipulator. Each washing zone is coupled to at least one wash element comprising at least one nozzle for connection to a first fluid pump for pumping washing fluid through the nozzle to generate a fluid jet and at least one deflector surface positioned to deflect the fluid jet towards the washing zone. The deflector surface is shaped to broaden the fluid jet so as to wash an outside surface of the at least one fluid manipulator residing in the washing zone.

In accordance with another embodiment of the invention, an automated system for the automated manipulation of fluids is provided comprising one or more reusable fluid manipulators for manipulating fluids; one or more wash stations for washing the one or more fluid manipulators described herein; a moving mechanism for moving the one or more fluid manipulators relative to the one or more wash stations and relative to the cavity, and a first fluid pump for generating the fluid jet for washing the outside surface of the fluid manipulator.

In accordance with yet another embodiment of the invention, a process for washing one or more reusable fluid manipulators of an automated system for the automated manipulation of fluids is provided comprising moving at least a portion of at least one fluid manipulator in a washing zone for washing the one or more fluid manipulators; generating a fluid jet of washing fluid; and directing the fluid jet onto a deflector surface shaped to broaden and deflect the fluid jet towards the washing zone so as to wash an outside surface of the fluid manipulator residing in the washing zone.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 1b shows in more detail some of the components of the system of FIG. 1a;

Figure 1A:
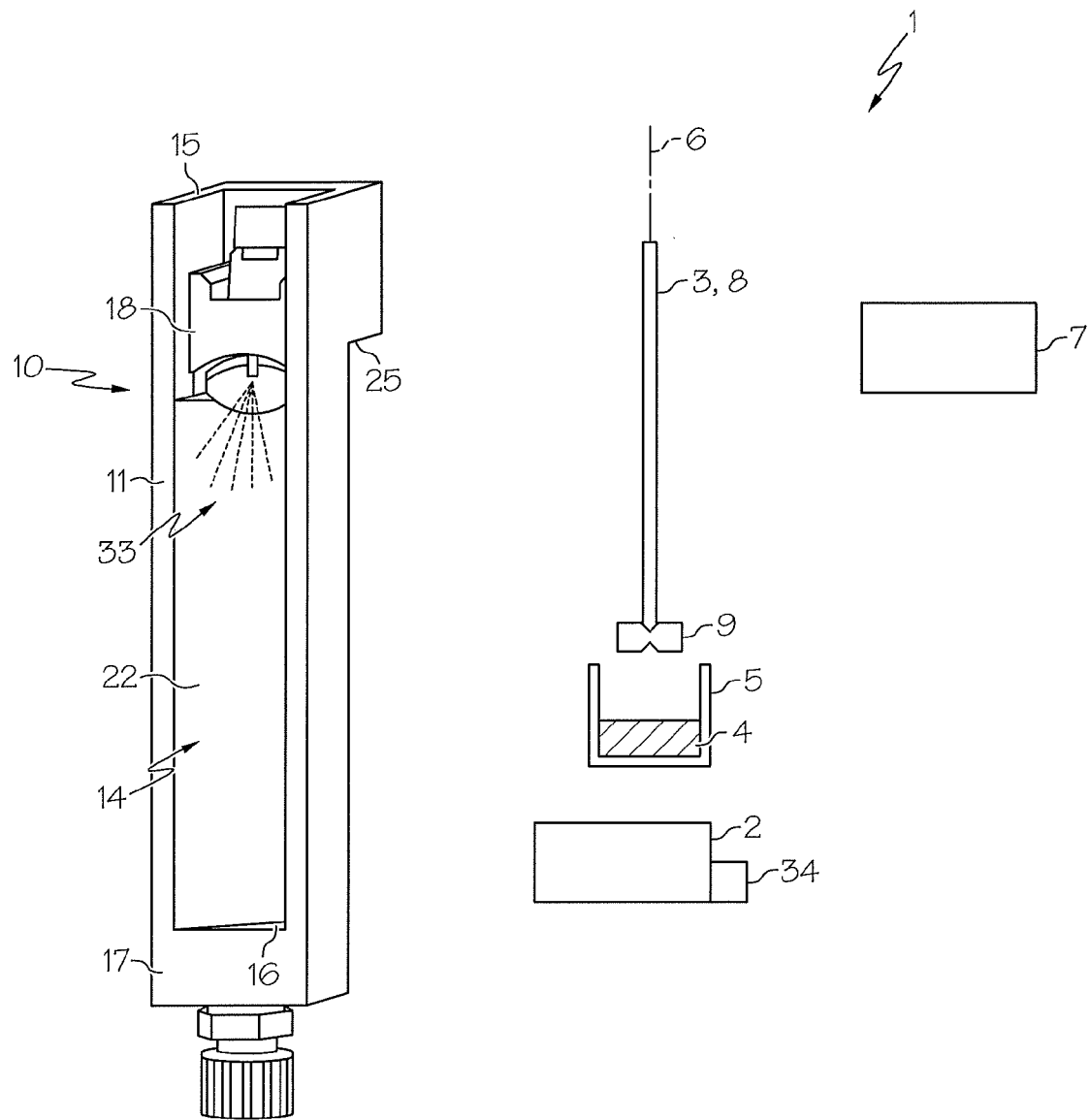
FIG. 1a is a partly sectioned perspective view for illustrating an exemplary system of the invention.

Skilled artisans appreciate that the elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

As used herein, the term "fluid" generally refers to biological and non-biological (chemical) fluids. Biological fluids comprise body fluids such as blood, serum, urine, plasma, milk, saliva, cerebrospinal fluids, nucleic acid containing fluids and the like and can, e.g., be subject to one or more analyses and assays in medical and pharmaceutical research and diagnosis. Non-biological fluids comprise drugs and chemical compounds such as reagents. Specifically, reagents are solutions for mixing with samples containing one or more analytes to obtain a detectable change in response to the analytes contained therein. In the more strict sense of the term, reagents include substances which can react with those analytes. Reagents, however, can also be non-reacting fluids such as buffers and diluting fluids.

As used herein, the term "washing fluid" refers to fluids commonly used with automated clinical analyzers, e.g., aqueous solutions to which specific substances such as detergents, salts, preservatives and solubilizers have been added. In general, water or other polar or non-polar solvent, with or without any additives may be used as a washing fluid.

As used herein, the term "fluid manipulator" refers to any object which can be used for physically manipulating fluids as long as manipulation of the fluids requires an outside or outer surface thereof to be brought in contact with the fluids.

According to various embodiments of the invention, a new wash element for washing one or more reusable fluid manipulators for manipulating fluids is provided. In some embodiments, the reusable fluid manipulator is a reusable pipette for pipetting fluids. In some embodiments, the reusable fluid manipulator is a reusable stirrer such as a rotatable paddle, for stirring fluids.

In some embodiments, the wash element of the invention comprises at least one nozzle for connection to a fluid pump for pumping washing fluid through the nozzle. The fluid pump can be used to forcibly dispense washing fluid through an opening of the nozzle to generate a fluid jet leaving the nozzle. In some embodiments, the wash element further comprises at least one deflector surface operatively coupled to the nozzle in a manner to deflect the fluid jet impinging on the deflector surface towards a spatial area, in the following denoted as "washing zone", located adjacent the deflector surface. The washing zone is sized to receive at least a portion of at least one fluid manipulator to be washed. Specifically, the deflector surface is shaped to deflect and broaden the fluid jet in a manner to wash an outside of the at least one fluid manipulator residing in the washing zone.

Generally, the deflected fluid jet can have any characteristics as, e.g., given by its dimensions, shape and streaming pressure according to the specific demands of the user. In some embodiments, the deflected fluid jet is specifically adapted to the one or more fluid manipulators to be washed. In some embodiments, the deflector surface is shaped to broaden the fluid jet in a fan-shaped manner. In some embodiments, the deflector surface is shaped to broaden the fluid jet in a cone-shaped manner. In some embodiments, the deflector surface is shaped to spray the fluid jet. In some embodiments, the deflector surface is formed by a concave recess. In some embodiments, the deflector surface is formed by a concave triangular hollow. In some embodiments, the deflector surface is formed by a convex cap. In some embodiments, the deflector surface is formed by a rounded tip.

Accordingly, in the wash element of the present invention, the fluid jet leaving the nozzle is being deflected by the deflector surface and targeted at the washing zone for washing the outer surface of at least one fluid manipulator, that is to say, of at least a portion thereof residing in the washing zone. Hence, the fluid jet is indirectly targeted at the at least one fluid manipulator. The wash element of the invention advantageously allows for an easy and reliable washing of the outside of the one or more fluid manipulators.

In some embodiments, the nozzle is integrally formed with the deflector surface enabling the wash element to be easily produced at low cost, e.g., using conventional moulding techniques such as injection moulding.

In some embodiments, the nozzle and/or the deflector surface are removably fixed to a mount so that the nozzle and/or the deflector surface can readily be replaced by another nozzle and deflector surface, respectively. In some embodiments, the mount of the wash element is adapted for removably fixing each one of a plurality of nozzles different with respect to each other. The various nozzles can, e.g., differ in nozzle parameters such as size of a nozzle port and shape of a nozzle duct conducting the wash fluid inside the nozzle so as to influence specific characteristics of the generated fluid jet impinging on the deflector surface. Accordingly, the nozzle of the wash element can readily be replaced by another nozzle in order to adapt the nozzle to the specific needs for washing the one or more fluid manipulators.

In some embodiments, the mount of the wash element is adapted for removably fixing each one of a plurality of various deflector surfaces. The various deflector surfaces can, e.g., differ in specific surface parameters such as shape and size so as to influence characteristics of the deflected fluid jet. Accordingly, the deflector surface of the wash element can readily be replaced by another deflector surface so that the deflector surface can advantageously be adapted to the specific needs for washing the one or more fluid manipulators.

In some embodiments, the mount of the wash element is adapted for removably fixing the nozzle and the deflector surface in various inter-distances with respect to each other. Accordingly, the characteristics of the deflected fluid jet can advantageously be adapted to the specific needs for washing the one or more fluid manipulators.

In some embodiments, the mount of the wash element is adapted for removably fixing the nozzle and/or the deflector surface in various positions relative to the mount. Hence, the nozzle and/or the deflector surface can, e.g., have various inclinations relative to the mount so as to adapt the characteristics of the deflected fluid jet to the specific needs for washing the one or more fluid manipulators.

In some embodiments, in which the one or more fluid manipulators are configured to be elongated objects, the nozzle is being adapted to generate a fluid jet parallel with respect to the extension of one or more fluid manipulators. In some alternative embodiments, in which the one or more fluid manipulators are elongated objects, the nozzle is being adapted to generate a fluid jet impinging on the deflector surface inclined with respect to the extension of one or more fluid manipulators.

According to the invention, a new wash station for washing one or more reusable fluid manipulators of an automated system for the automated manipulation of fluids is provided.

In some embodiments, the wash station comprises a cavity for inserting the one or more fluid manipulators having one or more washing zones, each of which being sized to receive at least a portion of at least one fluid manipulator. Accordingly, an outside of at least a portion of at least one fluid manipulator can be washed in the cavity. In some embodiments, the cavity is formed by an open-top casing, e.g., having a cup-like structure. In some embodiments, the cavity is formed by a closed casing provided with at least one top opening for inserting the one or more fluid manipulators.

In some embodiments, each of the washing zones is being operatively coupled to at least one wash element comprising at least one nozzle for connection to a first fluid pump for pumping washing fluid through the nozzle to generate a fluid jet and at least one deflector surface positioned to deflect the fluid jet towards the washing zone. The deflector surface is shaped to broaden the fluid jet so as to wash the outside of the at least one fluid manipulator residing in the washing zone. The one or more wash elements of the wash station of the present invention can be configured according to any one of the above-detailed embodiments. In order to avoid repetitions, reference is made to the above remarks made in connection with the wash element of the invention. In some embodiments, at least one washing zone is being operatively coupled to one wash element. In some embodiments, at least one washing zone is coupled to plural wash elements.

In some embodiments, the wash station comprises at least one fluid outlet or port opening into the cavity for removing waste fluid generated in the progress of washing the one or more fluid manipulators from the cavity.

Accordingly, in the wash station of the present invention, the one or more fluid manipulators can be brought in a position where at least a portion thereof resides in the washing zone. The wash station can readily be integrated in existing automated clinical analyzers for analyzing fluid samples so as to wash the outside of the one or more fluid manipulators.

In some embodiments, the at least one wash element is connected to a second fluid pump for pumping drying fluid through the nozzle to generate a fluid jet of drying fluid towards the wash zone.

In some embodiments, the cavity comprises one or more drying zones, each of which being sized to receive at least a portion of at least one fluid manipulator, each drying zone being coupled to at least one drying element comprising at least one nozzle for connection to a second fluid pump for pumping drying fluid through the nozzle to generate a fluid jet of drying fluid towards the drying zone.

In some embodiments, the wash station of the present invention comprises a plurality of wash elements specifically adapted to various fluid manipulators different with respect to each other. The wash station thus advantageously enables different fluid manipulators to be washed effectively. Accordingly, the volume of waste fluid can advantageously be reduced.

In some embodiments, the wash station of the present invention comprises a plurality of wash elements and/or drying elements at least some of which are similar or different with respect to each other so as to adapt the wash elements and/or drying elements to the specific needs for washing and/or drying various fluid manipulators.

In some embodiments, the one or more wash elements and/or drying elements are removably fixed to a mount enabling the wash elements to be readily replaced by other wash elements and/or drying elements. In some embodiments, a cavity forming casing is used for removably fixing the one or more wash elements and/or drying elements.

In some embodiments, the mount of the wash station is adapted for removably fixing each one of a plurality of wash elements and/or drying elements different with respect to each other. The various wash elements and/or drying elements may differ in nozzles and/or deflector surfaces and/or in relative positions with respect to each other and/or with respect to the mount. In particular, a drying element may comprise or not comprise a deflecting surface. Accordingly, the characteristics of the deflected fluid jets can advantageously be adapted to the specific needs for washing and/or drying various fluid manipulators. In some embodiments, the mount of the wash station is adapted for removably fixing each one of a plurality of wash elements and/or drying elements different with respect to each other in various positions relative to the mount. Accordingly, the characteristics of the deflected fluid jets can advantageously be adapted to the specific needs for washing and/or drying the various fluid manipulators.

The wash station of the present invention advantageously allows for an easy and reliable washing of one or more fluid manipulators which can be similar or different with respect to each other. Since the deflected fluid jets can readily be adapted to the specific washing needs of the various fluid manipulators, the consumption of washing fluid can advantageously be reduced.

According to various embodiments of the invention, a new system for the automated manipulation of fluids is provided. The system can be configured in various ways in accordance with specific demands of the user. It is particularly suitable for analyzing biological fluids but will also be useful with a wide variety of non-biological fluids as long as analysis thereof involves that fluids be manipulated by one or more reusable fluid manipulators such as pipettes and stirrers, respectively. The system of the invention may, e.g., be related to immunochemical and clinical-chemical analysis items. In some embodiments, the system of the invention is configured as clinical analyzer.

In some embodiments, the system comprises one or more reusable fluid manipulators such as pipetting tips and stirrers for manipulating fluids.

In some embodiments, the system comprises one or more wash stations for washing the one or more fluid manipulators.

In some embodiments, each of the wash stations comprises a cavity for inserting the one or more fluid manipulators having one or more washing zones, each of which being sized to receive at least a portion of at least one fluid manipulator. In some embodiments, the cavity is configured for insertion of one fluid manipulator. In some embodiments, the cavity is configured for insertion of plural fluid manipulators which can be of similar or different type with respect to each other.

In some embodiments, each of the one or more washing zones is being operatively coupled to at least one wash element having at least one nozzle connected to a first fluid pump for pumping washing fluid through the nozzle to generate a fluid jet and at least one deflector surface positioned to deflect the fluid jet towards the washing zone, wherein the deflector surface is being shaped to broaden the fluid jet so as to wash an outside of the at least one fluid manipulator residing in the washing zone. In some embodiments, a nozzle of a washing element may be connected to a second fluid pump for pumping drying fluid through the nozzle to generate a fluid jet of drying fluid towards the wash zone.

In some embodiments, the cavity comprises one or more drying zones, each of which being sized to receive at least a portion of at least one fluid manipulator, each drying zone being coupled to at least one drying element comprising at least one nozzle for connection to a second fluid pump for pumping drying fluid through the nozzle to generate a fluid jet of drying fluid towards the drying zone. The wash station and the one or more wash elements and/or drying elements can be configured according to any one of the above-detailed embodiments. In order to avoid repetitions, reference is made to the remarks made above in connection with the wash element and the wash station, respectively, of the invention. In some embodiments, the one or more wash stations are related to one type of fluid manipulator. In some embodiments, plural wash stations are related to various types of fluid manipulators different with respect to each other. Specifically, one wash station can be related to one type of fluid manipulators such as pipettes and another wash station can be related to another type of fluid manipulators such as stirrers. Specifically, in some embodiments, each wash station is related to an individual type of fluid manipulators which can be similar or different with respect to each other. In some embodiments, one or more washing zones of one washing station are related to one type of fluid manipulator. In some embodiments, one or more washing zones of one washing station are related to various types of fluid manipulators different with respect to each other. In the system according to various embodiments of the present invention, the first fluid pump can be used for generating at least one fluid jet of washing fluid directed to the deflector surface operatively coupled thereto for deflecting the fluid jet towards the washing zone. In some embodiments, the first fluid pump communicates with a reservoir containing the washing fluid. Basically, fluid pumps capable of pumping washing fluid through the nozzle can be used in the system of the invention. In some embodiments, the first fluid pump is a pump of the rotary displacement pump type such as a gearwheel pump.

In some embodiments, the system further comprises a moving mechanism for moving the one or more fluid manipulators relative to the one or more wash stations and relative to the cavity of the one or more work stations so that at least a portion thereof resides in the washing zone. For the present invention it is typical that the moving mechanism is capable of performing movements having at least components of vertical translational movements so as to vertically move the one or more fluid manipulators. In some embodiments, the moving mechanism is also capable of performing horizontal translational movements so as to move the one or more fluid manipulators in horizontal directions. In some embodiments, the moving mechanism is also capable of performing rotational movements so as to turn the one or more fluid manipulators. In some embodiments, the moving mechanism is also capable of performing fast rotational movements so as to centrifuge the one or more fluid manipulators about themselves. In some embodiments, the moving mechanism is a robotic arm. In some embodiments, the moving mechanism comprises components of movement in two directions of travel in a horizontal plane and a third direction of travel vertical thereto as, e.g., can be realized by a beam-translation mechanism.

The system further comprises a first fluid pump for generating the fluid jet for washing the outside of the fluid manipulator.

In some embodiments, the system comprises a second fluid pump for generating a fluid jet of drying fluid for drying the outside of the fluid manipulator.

In some embodiments, the second fluid pump communicates with a reservoir containing the drying fluid. Basically, fluid pumps capable of pumping gas through the nozzle can be used in the system of the invention. A drying fluid may be, e.g., air, nitrogen or other gas.

In some embodiments, the system comprises a controller set up to control washing the one or more fluid manipulators including control of the moving mechanism in a manner that each of the fluid manipulators is inserted in the cavity of one or more wash stations so that at least a portion thereof resides in the washing zone and control of the first fluid pump so that the fluid jet of washing fluid is generated for washing the outside of the fluid manipulator.

In some embodiments, the controller is set up to control washing the fluid manipulators in such a manner that at least one fluid manipulator is moved from one washing zone to one or more other washing zones of one washing station. In some embodiments, the controller is set up to control washing the fluid manipulators in such a manner that at least one fluid manipulator is moved from one washing zone to one or more other washing zones of plural washing stations. In some embodiments, the controller is set up to control moving the fluid manipulators in such a manner that at least one fluid manipulator is turned simultaneously with generating the fluid jet so that each side of the fluid manipulator can effectively be washed. In some embodiments, the controller is set up to control moving the fluid manipulators in such a manner that, after washing a first portion of at least one fluid manipulator in a washing zone, one or more second portions of the fluid manipulator different from the first portion are moved into the washing zone for washing by the washing fluid.

In some embodiments, the controller is set up to control the moving mechanism in such a manner to centrifuge the fluid manipulator about itself in order to remove washing fluid wetting the fluid manipulator after washing.

In some embodiments, the controller is set up to control a second fluid pump so that a fluid jet of drying fluid is generated for drying the outside of the fluid manipulator and optionally to control the moving mechanism in such a manner that at least one fluid manipulator is moved from one washing zone to a drying zone where the fluid jet of drying fluid is generated.

According to a typical embodiment of the present invention, the controller is set up to control the moving mechanism in such a manner to centrifuge the fluid manipulator about itself and to control a second fluid pump so that a fluid jet of drying fluid is generated for drying the outside of the fluid manipulator. The combination of centrifuging and fluid jet of drying fluid achieves an even more efficient drying after washing.

In general, drying the fluid manipulator after washing is advantageous since it can be prevented that traces of washing fluid on the fluid manipulator after washing are introduced into the fluid being manipulated, causing possible contamination and/or dilution.

Contrary to the prior art solutions mentioned herein, the system of the present invention advantageously allows for an easy, reliable and effective washing of one or more fluid manipulators which can be similar or different with respect to each other. Due to effectively washing the fluid manipulators, and especially in light of the fact that two or more fluid manipulators can be washed in one cavity, the consumption of washing fluid can advantageously be reduced.

According to the various embodiments of the present invention, a new process for washing one or more reusable fluid manipulators of an automated system for the automated manipulation of fluids is provided. In some embodiments, the process is implemented by the above-described system of the invention. Hence, in some embodiments, the process includes a step of providing a system as-above described which may be embodied according to any one or any combination of the above-described embodiments.

In some embodiments, the process comprises a step of moving at least a portion of at least one fluid manipulator in a washing zone configured for washing the one or more fluid manipulators.

In some embodiments, it comprises a step of generating a fluid jet of washing fluid and directing the fluid jet onto a deflector surface shaped to broaden and deflect the fluid jet towards the washing zone so as to wash the outside of the fluid manipulator residing in the washing zone.

In some embodiments, the process comprises a step of turning the at least one fluid manipulator simultaneously with generating the fluid jet.

In some embodiments, the process comprises a step in which, after washing a first portion of the at least one fluid manipulator, one or more second portions of the fluid manipulator different from the first portion are moved into the washing zone for washing by the washing fluid.

In some embodiments, the process comprises the step of centrifuging the fluid manipulator about itself for removing washing fluid wetting the fluid manipulator after washing.

In some embodiments, the process comprises the step of generating in a washing zone or drying zone a fluid jet of drying fluid for drying the fluid manipulator after washing.

In some embodiments, the process comprises a step of moving at least a portion of the at least one fluid manipulator in a first washing zone for washing an outside surface thereof and then moving it to one or more second washing zones different from the first washing zone for washing an outside surface thereof. Specifically, in some embodiments, at least a portion of at least one fluid manipulator is moved from one washing zone formed by one washing station to one or more other washing zones formed by the same washing station or by one or more other washing stations.

In some embodiments, the process comprises a step of replacing the nozzle of the washing zone and/or drying zone by another nozzle different from the former one and/or by replacing the deflector surface of the washing zone and/or drying zone by another deflector surface different from the former one depending on the fluid manipulator.

The various embodiments of the invention may be used alone or in any combination thereof without departing from the scope of the invention.

By way of illustration, specific exemplary embodiments in which the invention may be practiced now are described. In this regard, terminology with respect to orientations and directions such as "horizontal", "vertical", "upper", "lower", "above" and "below" is used with reference to the orientations of the figures being described. Because components described can be positioned in a number of different orientations, this terminology is used for the purpose of illustration only and is in no way limiting.

Reference is first made to FIGS. 1 to 4. Accordingly, in some embodiments, a system for the automated manipulation of fluids 4, generally referred to at reference numeral 1, to be used for the analysis of samples comprises one or more analytical units 2 related to clinical-chemical and/or immunochemical analysis items. While only one analytical unit 2 is schematically shown in FIG. 1a for the purpose of illustration only, it is to be appreciated that the system 1 can contain more than one analytical unit 2 according to the specific demands of the user. Since the detailed mechanism of the analytical method is not relevant for the understanding of the present invention, it is not further elucidated herein.

It, however, is relevant for the invention that analysis of the samples can involve physical manipulation of fluids 4 such as samples and reagents by at least one reusable fluid manipulator 3, the outside of which is temporarily brought in contact with the fluids. As illustrated, in some embodiments, the fluid manipulator 3 is configured as a reusable stirrer for stirring fluids such as reagents which have to be homogenized before use, such as, e.g., suspensions of magnetic beads. Specifically, in some embodiments, the stirrer comprises an elongated rod 8 provided with a paddle 9 on its lower end adapted for stirring fluids when turning the rod 8 around its longitudinal axis 6. While only one fluid manipulator 3 is shown for the purpose of illustration only, it is to be understood that the system 1 can comprise more than one fluid manipulator 3, e.g., configured as pipettes for pipetting fluids.

Figure 1B:
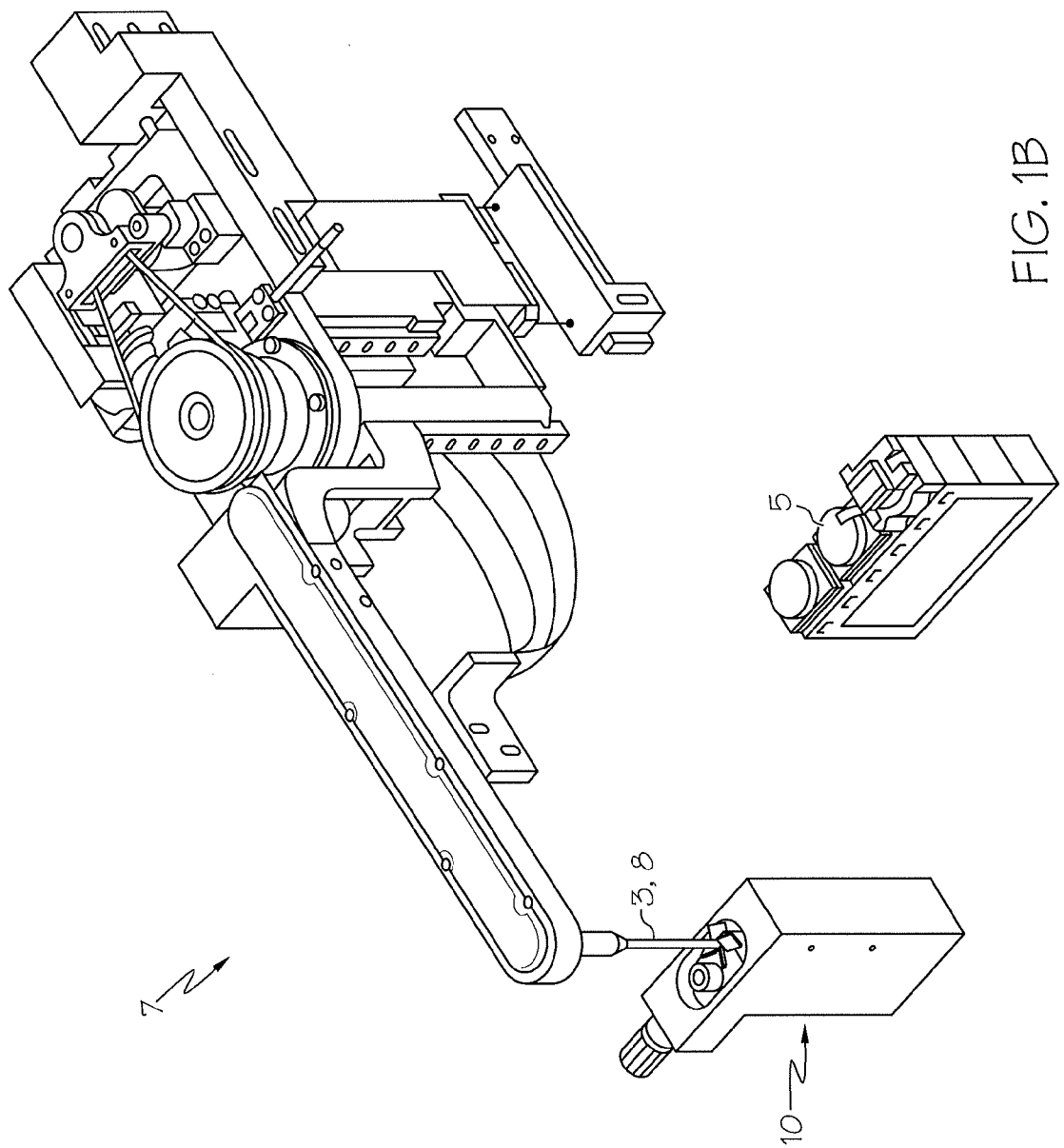

With continued reference to FIG. 1a and as further elucidated in FIG. 1b, as is commonplace in the prior art, in some embodiments, the system 1 uses one or more open-top vessels 5 sized to receive fluids 4 for their manipulation.

With yet continued reference to FIG. 1a and as further elucidated in FIG. 1b, in some embodiments, the fluid manipulator 3 is operatively coupled to a moving mechanism 7 for moving the at least one fluid manipulator 3 relative to a ground plate (not illustrated). As shown in FIG. 1b, the moving mechanism 7 is configured as a beam-translation mechanism having components of movement in two directions of travel in a horizontal plane provided with a transfer head moveable in a third direction of travel towards and away from the horizontal plane. Such moving mechanisms are however commonplace in automated clinical analyzers known in the prior art and different variations are possible.

For the present invention it is typical that the moving mechanism 7 can perform movements including at least components of vertical translational movements so as to vertically move the fluid manipulator 3 in vertical direction. Accordingly, the fluid manipulator 3 can selectively be lowered into and lifted out of the fluids 4 being manipulated. Configuring the fluid manipulator 3 as a stirrer, it is useful that the moving mechanism 7 can rotate the fluid manipulator 3 around its longitudinal axis 6 so as to stir fluids by the rotated paddle 9.

The fluid manipulator 3 of the system 1 has to be washed in-between consecutive fluid manipulations in order to avoid carry-over and cross-contamination of the fluids 4. In some embodiments, the system 1 includes one or more wash stations 10 for washing the fluid manipulator 3. As can be taken from a perspective upper view of FIG. 2, in some embodiments, the wash station 10 includes a block-like station body 11 disposed in an upright vertical position like a tower. The station body 11 has a bottom-sided portion 17 provided with two opposing body flanges 12 serving as platform for removably attaching the station body 11 to the ground plate. Specifically, each of the body flanges 12 has at least one through-hole 13 so that a fixing means (not illustrated) such as a screw or bolt can be brought in fixing engagement with the ground plate.

Figure 2:
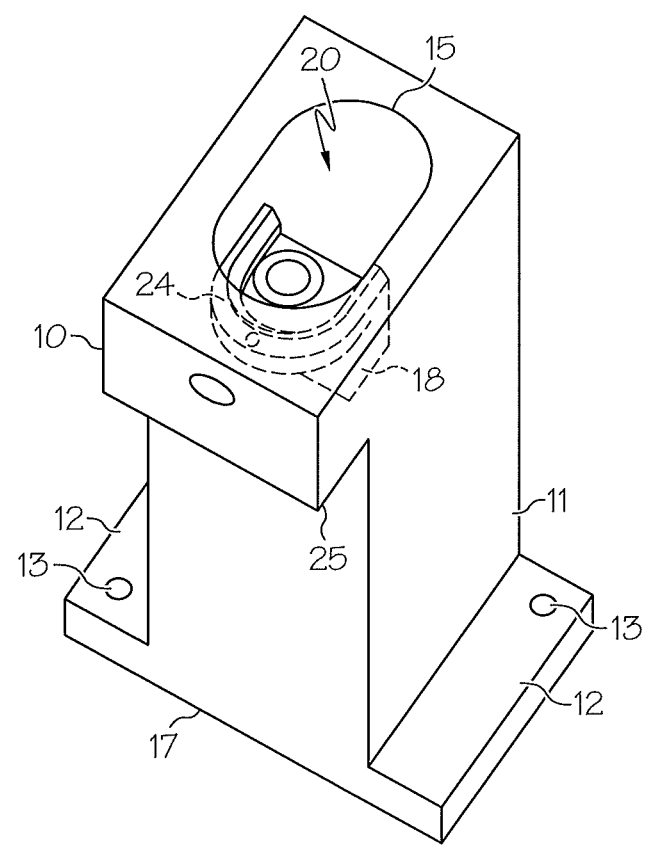
FIG. 2 is a perspective view of a wash station similar to that of the system of FIG. 1.

The station body 11 forms a cavity 14 which, with continued reference to FIGS. 1a-2, in some embodiments, is essentially oblate-cylindrical in shape. The cavity 14 has a top opening 15 which, in some embodiments, corresponds to the horizontal cross-section of the cavity 14. As illustrated, in some embodiments, a vertically oriented fluid outlet 16 penetrating the bottom portion 17 of the body 11 opens into the cavity 14. In some embodiments, the station body 11 is made of one piece and can, e.g., be manufactured via injection molding or any other technique of the molding type.

With continued reference to FIGS. 1a-2, in some embodiments, a wash element 18 for washing the fluid manipulator 3 is inserted in the cavity 14 somewhat below the top opening 15. As drawn to a larger scale in FIGS. 3A-3B, in some embodiments, the wash element 18 comprises an element body 19 which has a vertically sectioned oblate-cylindrical outer shape so as to closely fit into the cavity 14 but leaving a free space 20 between a planar front-sided surface 21 of the element body 19 and an inner wall 22 forming the cavity 14. The planar surface 21 defines a front-side of the wash element 18.

Figure 3A:
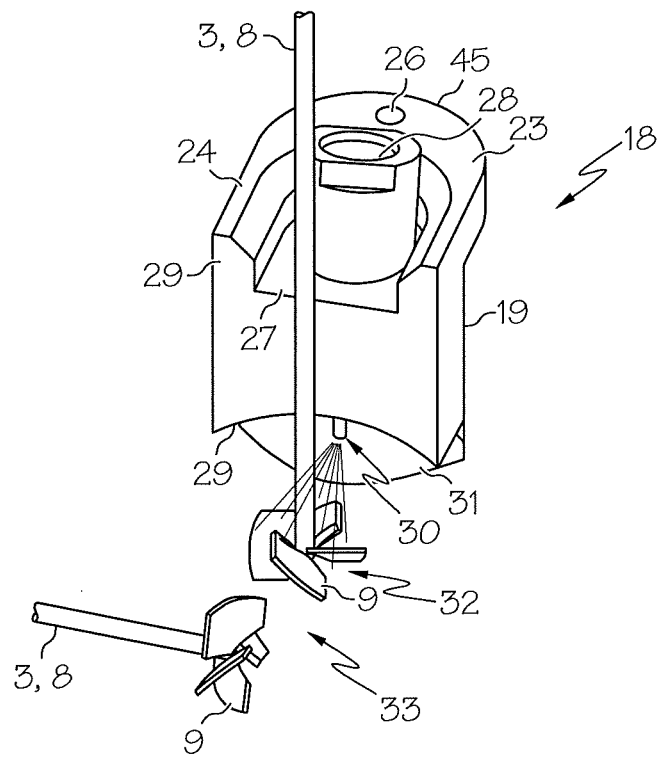
FIGS. 3A-3B are different perspective views of the wash element of the wash station of the system of FIG. 1.
Figure 3B:
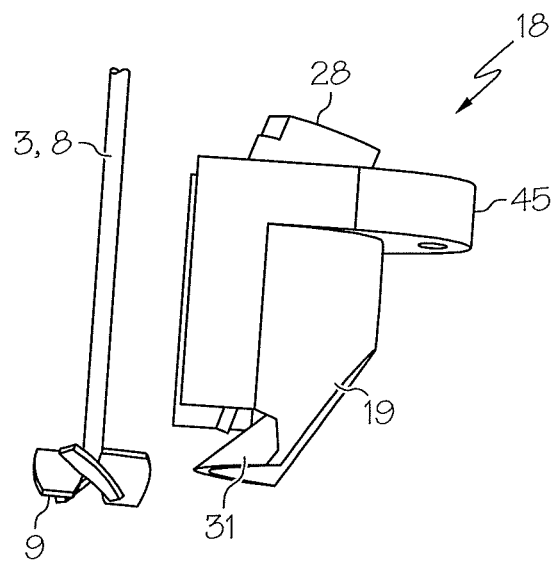

With continued reference to FIGS. 3A-3B, in some embodiments, an upper surface 23 of the element body 19 forms an upright collar 24 projecting off the element body 19 in opposite relationship with respect to the planar front-sided surface 21 forming an essentially semi-circular collar 45 on a back-side of the wash element 18 relative to the front-side as defined by the planar front-sided surface 21. As illustrated in FIGS. 1-2, in some embodiments, when inserting the wash element 18 into the cavity 14, the collar 24 can be brought in a position where it rests on a shoulder 25 formed by the inner wall 22 of the cavity 14 to then be removably fixed by conventional fixation means 26 such as a screw.

With continued reference to FIGS. 3A-3B, in some embodiments, the collar 24 surrounds a planar portion 27 of the upper surface 23 provided with a vertically projecting connector 28 for connection to a washing fluid supply line (not illustrated) for supplying washing fluid. As illustrated, in some embodiments, the connector 28 can be adapted to fix the washing fluid supply line by means of conventional fixation mechanism such as a luer lock turning mechanism.

With continued reference to FIGS. 3A-3B, in some embodiments, a lower surface 29 of the element body 19 is convex-shaped with respect to an upward direction. Furthermore, the lower surface 29 is provided with a nozzle 30 directed towards a deflector surface 31 formed by a convex cap arranged below the lower surface 29. The connector 28 is fluidically connected to the nozzle 30 by an internal fluid duct (not illustrated) formed by the element body 19 so that washing fluid supplied to the connector 28 can be forcibly dispensed by the nozzle 30 to generate a fluid jet 32 schematically illustrated in FIGS. 3A-3B. In some embodiments, the washing fluid supply line is fluidically connected to a fluid pump communicating with a reservoir containing washing fluid for pumping washing fluid through the nozzle 30.

With continued reference to FIGS. 3A-3B, in some embodiments, the deflector surface 31 is positioned to deflect the impinging fluid jet 32 towards the front-side of the washing element 18. Stated more particularly, the deflector surface 31 is shaped to generate a broadened fluid jet 32, e.g., broadened in a fan-shaped manner, to thereby form a washing zone 33 within the cavity 14 for washing the fluid manipulator 3. In some embodiments, the element body 19 is made of one piece and can, e.g., be manufactured via injection molding or any other technique of the molding type.

In general, the fluid manipulator 3 can have any orientation with respect to the wash element 18 and nozzle 30, respectively. As illustrated in FIG. 3A, in some embodiments, the nozzle 30 is in parallel alignment with the longitudinal axis 6 of the fluid manipulator 3 at least with respect to a virtual plane accommodating both the nozzle 30 and the longitudinal axis 6. As further illustrated in FIG. 3A, in some embodiments, the nozzle 30 is inclined to the longitudinal axis 6 of the fluid manipulator 3 to, e.g., form an angle of about 90° therebetween. Stated more particularly, a first virtual plane accommodating the nozzle 30 and a second virtual plane accommodating the longitudinal axis 6 are inclined with respect to each other.

Figure 4:
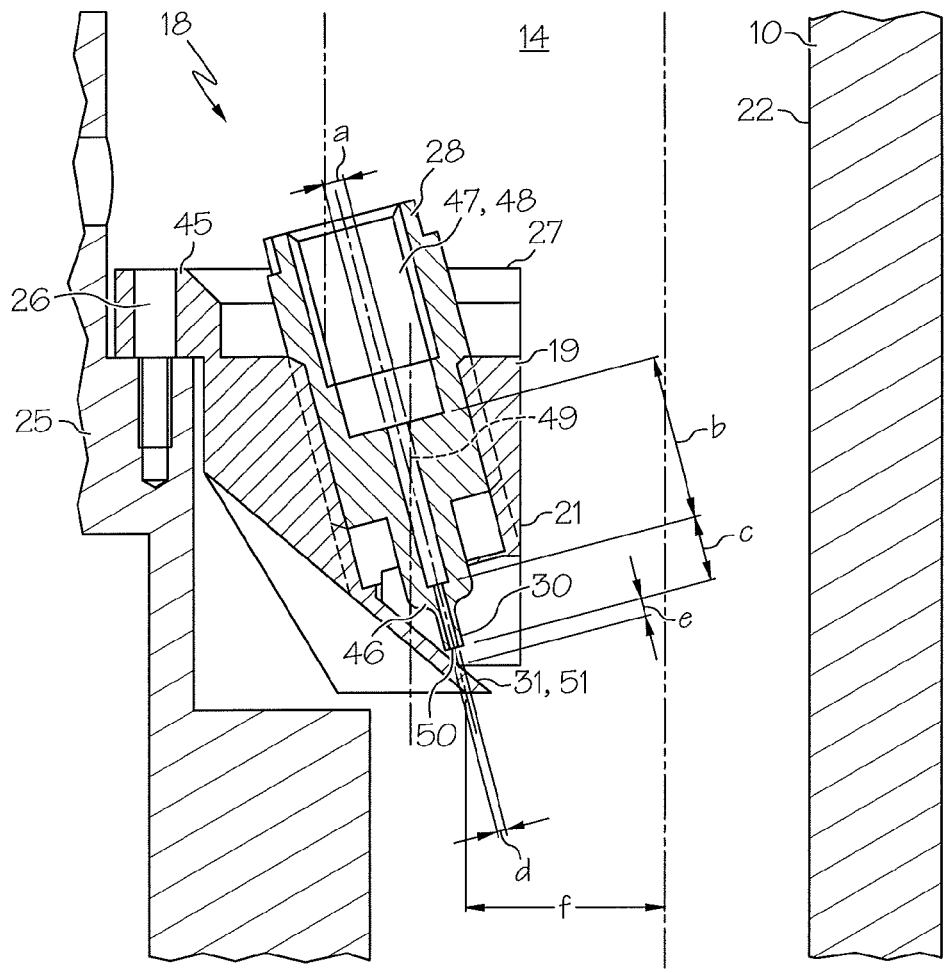
FIG. 4 is a sectional view illustrating the upper part of the wash station of FIG. 1.

With particular reference to FIG. 4, illustrating a sectional view of the upper part of the wash station 10, in some embodiments, the wash element 18 comprises a nozzle body 46 forming an inner space 47 comprised of three sections fluidically communicating with respect to each other: a first section 48 opening at the connector 28, a much smaller intermediate second section 49 and a yet smaller third section forming the nozzle 30 having a nozzle opening 50 for discharging the fluid jet 32. In some embodiments, the various sections 48, 49, 30 of the inner space 47 are cylindrical in shape. The fluid jet 32 leaving the nozzle 30 hits the deflector surface 31 at an impact location 51.

With continued reference to FIG. 4, in some embodiments: a diameter a of the second section 49 amounts to about 1.2 mm; a length b of the second section 49 amounts to about 9.5 mm; a diameter d of the nozzle 30 amounts to about 0.5 mm; a length c of the nozzle 30 amounts to about 3.5 mm; a distance e between the nozzle opening 50 and the impact location 51 amounts to about 1.35 mm; and a distance f between the impact location 51 and a center point of the paddle 9 located in the middle of the washing zone 33 amounts to about 11.5 mm. Those of skill in the art will appreciate that these are only exemplary values which can broadly vary according to the specific demands of the user.

With continued reference to FIG. 1a, in some embodiments, the system 1 further comprises a controller 34 set up to control washing the one or more fluid manipulators 3. In some embodiments, the controller 34 is configured as programmable logic controller running a machine-readable program provided with instructions to perform operations for washing the one or more fluid manipulators 3. Stated more particularly, the controller 34 is electrically connected to the components requiring control which comprise the fluid pump (not illustrated) connected to the connector 28 and the moving mechanism 7.

In order to avoid carry-over and cross-contamination, the one or more re-usable fluid manipulators 3 have to be washed in-between consecutive operations. With continued reference to FIG. 1, in some embodiments, starting the washing process, the fluid manipulator 3 is moved over the wash station 10 in a position right above the top opening 15 and then lowered into the cavity 14 adjacent the planar front-sided surface 21 so that the paddle 9 is located in the middle of the washing zone 33 in front of the deflector surface 31. The fluid manipulator 3 can readily be inserted into the cavity 14 through the free space 20. The fluid pump is operated to supply washing fluid to the connector 28 so as to generate the fluid jet 32 impinging on the deflector surface 31 which then is deflected onto the paddle 9 in a fan-shaped manner for washing the paddle 9. While generating the fluid jet 32, the paddle 9 can be turned within the washing zone 33 so that all sides of the paddle 9 can thoroughly be washed. The fluid manipulator 3 can then be moved upwards to perform the next stirring operation. Otherwise, e.g., in case of washing pipetting tips, in some embodiments, portions other than the washed portion thereof can be moved in the washing zone 33 for washing by the washing fluid.

Due to the fact that the cavity 14 is not filled with washing fluid, the cavity 14 of the washing station 10 can be made large to accommodate plural washing zones 33, each of which being operatively coupled to a nozzle 30 and a deflector surface 31 for generating a fluid jet 32 directed towards the washing zone. Accordingly, plural fluid manipulators 3 can simultaneously be washed in one cavity 14 to thereby save time and reduce the volume of waste fluid generated in the process of washing the fluid manipulators 3. Otherwise, one fluid manipulator 3 can once or repeatedly be moved to another washing zone of the same washing station 10. Alternatively or additionally, one fluid manipulator 3 can once or repeatedly be moved to another washing zone of another washing station. In general, plural wash stations 10 can be related to different types of fluid manipulators 3 and/or can be adapted to perform a washing process specifically adapted to the washing needs of one or more fluid manipulators 3.

In some embodiments, deionized water is used for washing the one or more fluid manipulators 3. The washing fluid used for washing the one or more fluid manipulators 3 leaves the cavity 14 through the bottom-sided fluid outlet 16 preventing that the cavity 14 is (e.g. fully) filled with washing fluid. Stated more particularly, the fluid outlet 16 is sized to let as much washing fluid as necessary pass through to prevent that the paddle 9 dips into washing fluid accumulating in the cavity 14. In some embodiments, the fluid outlet 16 is in fluid communication with a waste container (not illustrated) for accumulating the waste fluid. Accordingly, the paddle 9 is washed by washing fluid projected thereon via the deflector surface 31 of one or more washing zones 33. The cavity 14 prevents the surroundings of the wash station 10 from being contaminated by washing fluid.

Figure 5A:
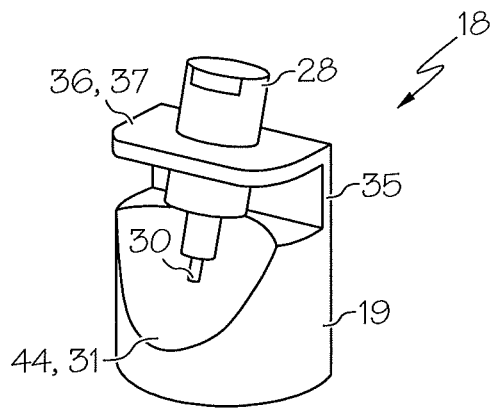
FIGS. 5A-5C are different perspective views of a first variant of the wash element of the wash station of the system of FIG. 1.
Figure 5B:
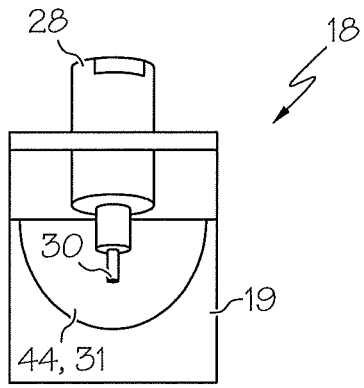
Figure 5C:
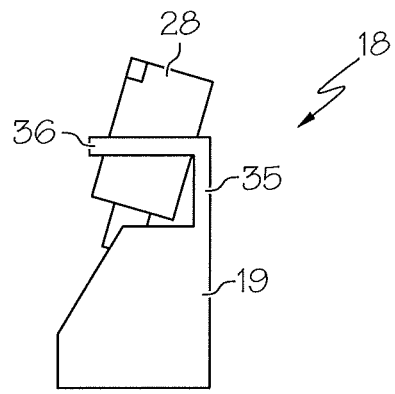

Reference is now made to FIGS. 5A-5C illustrating a variant of the wash element 18 of the wash station 10 of the system 1. In order to avoid repetitions, only differences with respect to the embodiment of FIGS. 3A-3B are explained and, otherwise, reference is made to the explanations made in connection with this embodiment. Accordingly, as illustrated, in some embodiments, the wash element 18 includes an element body 19 comprising an angled structure comprised of a vertical plate 35 and a horizontal plate 36. In some embodiments, the horizontal plate 36 is integrally formed with the connector 28 and the nozzle 30. In some embodiments, the deflector surface 31 is concave-shaped with respect to an upward direction formed by a concave recess 44. As illustrated in FIG. 3C, in some embodiments, the nozzle 30 is inclined relative to the deflector surface 31. Due to the concave-shaped deflector surface 31, the deflected fluid jet (not illustrated) of the wash element 18 of FIGS. 5A-5C is different from the fluid jet 32 of the wash element 18 of FIGS. 3A-3B.

Figure 6A:
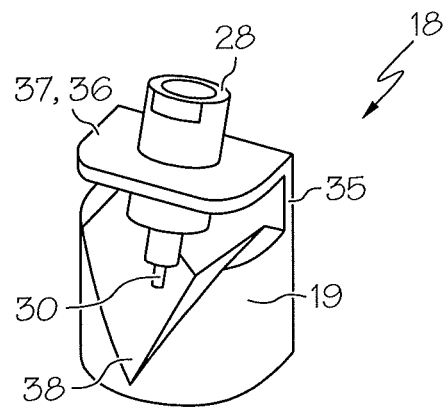
FIGS. 6A-6C are different perspective views of a second variant of the wash element of the wash station of the system of FIG. 1.
Figure 6B:
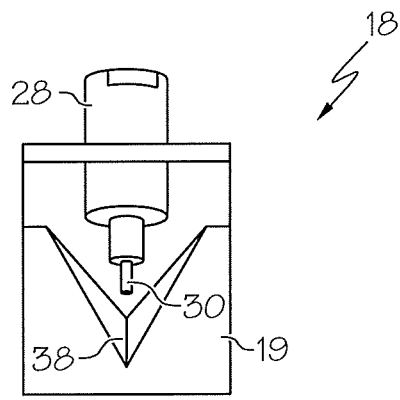
Figure 6C:
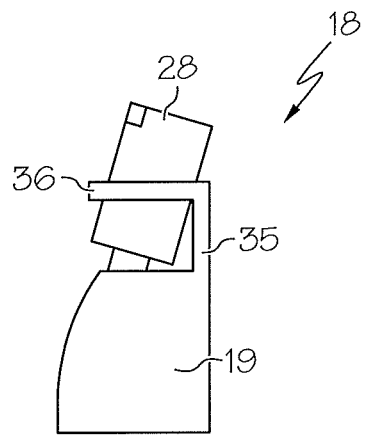

Reference is now made to FIGS. 6A-6C illustrating a further variant of the wash element 18 of the wash station 10 of the system 1. In order to avoid repetitions, only differences with respect to the embodiment of FIGS. 5A-5C are explained and, otherwise, reference is made to the explanations made in connection with this embodiment. Accordingly, as illustrated, in some embodiments, the deflector surface 31 is concave-shaped with respect to an upward direction formed by a concave hollow or chute 38. The deflector surface 31 comprises two angled portions 37 together forming the chute 38. The nozzle 30 is directed to the central (deepest) portion of the chute 38. Due to the deflector surface 31, the deflected fluid jet (not illustrated) of the wash element 18 of FIGS. 6A-6C is different from the fluid jet 32 of the wash element 18 of FIGS. 5A-5C.

Figure 7A:
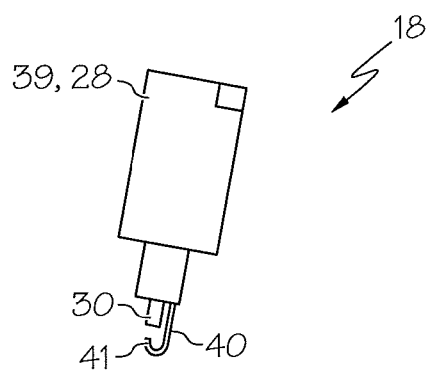
FIGS. 7A-7C are different perspective views of a third variant of the wash element of the wash station of the system of FIG. 1.
Figure 7B:
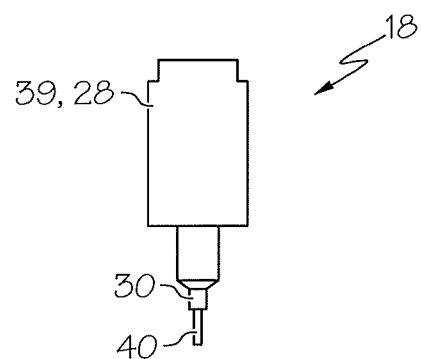
Figure 7C:
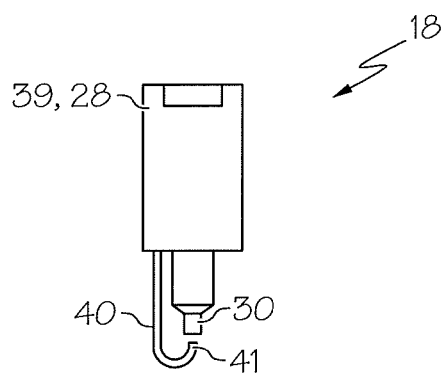

Reference is now made to FIGS. 7A-7C illustrating a yet further embodiment of the wash element 18 of the wash station 10 of the system 1. In order to avoid repetitions, only differences with respect to the embodiment of FIGS. 3A-3B are explained and, otherwise, reference is made to the explanations made in connection with this embodiment. Accordingly, as illustrated, in some embodiments, the wash element 18 includes an element body 19 comprising an essentially cylindrical body portion 39 for fixing in the cavity 14. On an upper side, the cylindrical body portion 39 can be connected to a washing fluid supply line for supplying washing fluid. On a lower side, the cylindrical body portion 39 forms the nozzle 30. The cylindrical body portion 39 further comprises a hook 40 provided with a rounded tip 41 on its free end acting as deflector surface 31 for the fluid jet (not illustrated). Specifically, the rounded tip 41 is positioned in a manner to spray or atomize the impinging fluid jet for washing the paddle 9. Due to the rounded tip 41, the deflected fluid jet of the wash element 18 of FIGS. 7A-7C is different from the fluid jet 32 of the wash element 18 of the former embodiments.

Figure 8:
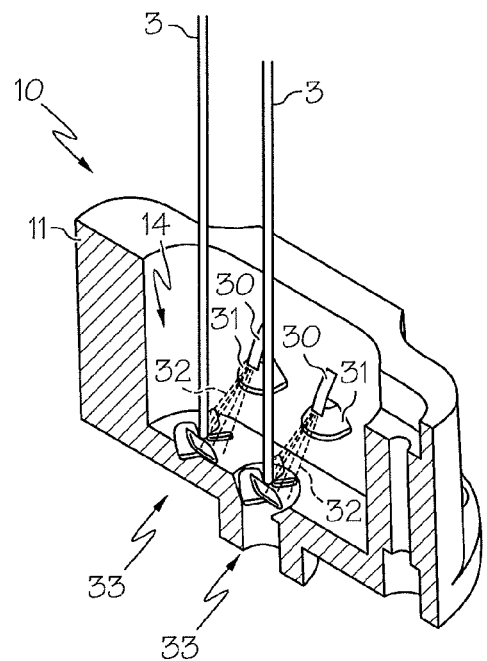
FIG. 8 is a perspective partly sectioned view depicting a variant of the wash station of the system of FIG. 1.

Reference is now made to FIG. 8 illustrating a variant of the wash station 10 of the system 1. In order to avoid repetitions, only differences with respect to the embodiment of FIGS. 1, 2, 3A-3B are explained and, otherwise, reference is made to the explanations made in connection therewith. Accordingly, as illustrated, in some embodiments, the wash station 10 has a larger cavity 14, the inner wall 22 of which forms two adjacent nozzles 30, each of which being operatively coupled to an individual deflector surface 31 for deflecting the fluid jets 32 leaving the nozzles 30 to thereby form two separate washing zones 33 in front of the deflector surfaces 31. As illustrated, in some embodiments, the deflector surfaces 31 are formed by the upper sides of semi-cylindrical protrusions projecting towards the inside of the cavity 14. In some embodiments, the deflector surfaces 31 are convex-shaped with respect to an upwards direction to broaden the deflected fluid jet 32, e.g., in a fan-shaped manner. Accordingly, the wash station 10 of FIG. 8 enables that two fluid manipulators 3 be simultaneously washed.

Accordingly, as can be taken from the above, the wash station 10 of the system 1 can be used to wash one or more fluid manipulators 3 simultaneously or consecutively providing for one or more wash elements 18. The wash elements 18 can specifically be adapted to the specific needs for washing the fluid manipulators 3 as, e.g., given by individual shapes and/or specific washing requirements of the fluid manipulators 3. Accordingly, the volume of washing fluid used for washing the fluid manipulators 3 can advantageously be saved. The wash station 10 and/or the wash elements 18 can readily be replaced by other wash station and wash elements, respectively, e.g., prior to starting the washing process, to adapt it to the specific washing needs of the fluid manipulators 3.

Figure 9:
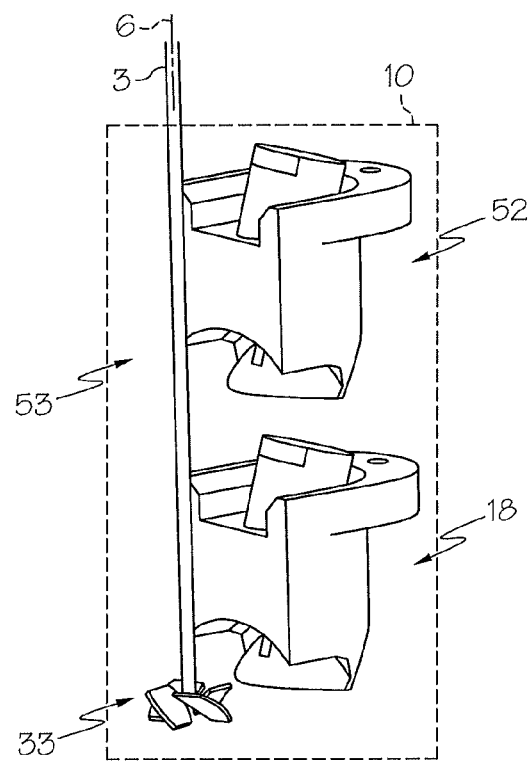
FIG. 9 shows an embodiment of the present invention wherein a drying element is arranged above a wash element.

Reference is now made to FIG. 9 illustrating a variant of the wash station 10 of the system 1. In particular, the wash station 10 comprises a drying element 52 arranged above a wash element 18 such as to dry the fluid manipulator 3 with a fluid jet of drying fluid after washing by the wash element 18. In this case, the wash element 18 and drying element 52 are structurally the same, wherein however, the wash element 18 is being connect to a first fluid pump (not shown) for pumping wash fluid and the drying element 52 is being connected to a second fluid pump (not shown) for pumping drying fluid. In operation, after washing of the fluid manipulator 3 in the washing zone 33, the fluid manipulator 3 is moved (not shown) to a drying zone 53 located above the washing zone 33. For an even better effect, drying by the drying element 52 is combined with centrifugation of the fluid manipulator, i.e., spinning about its longitudinal axis 6 at a higher number of revolutions per minutes compared to, e.g., a slower rotation during washing.

The drying element 52 may of course be structurally different from the wash element 18 and/or be differently arranged with respect to the wash element 18. According to one embodiment (not shown) the washing zone 33 and drying zone 53 are the same zone, wherein the wash element 18 also acts as a drying element 52, e.g., by connecting the first fluid pump and the second fluid pump to the same element and operating in sequence.

Figure 10:
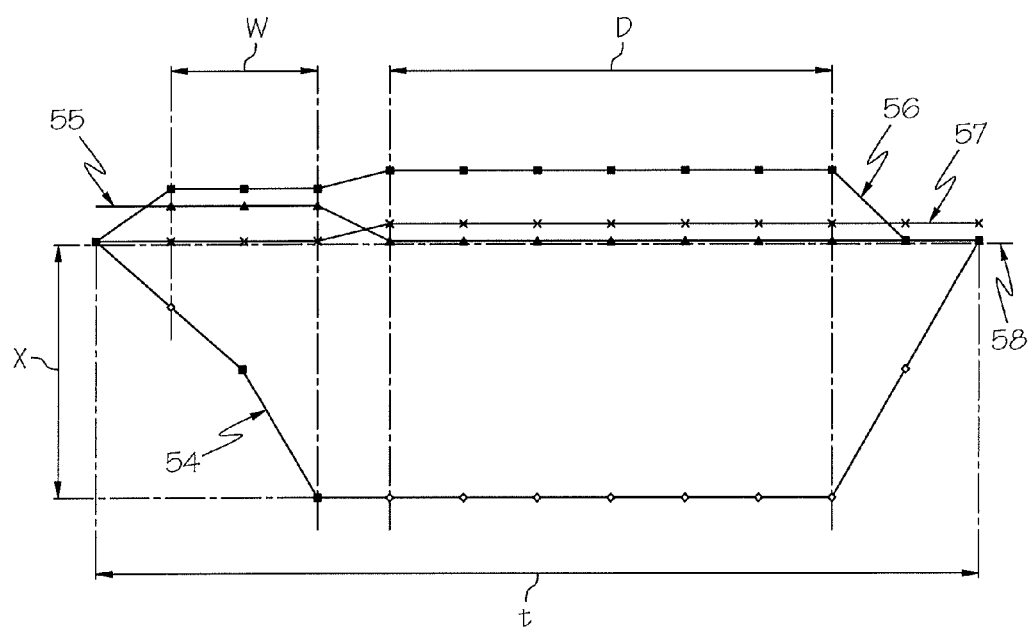
FIG. 10 provides an example of workflow.

FIG. 10 provides a schematic example of a workflow for the system 1 according to one embodiment. In particular, line 54 represents the position of the fluid manipulator 3 in the wash station 10, i.e., the distance of travel of the fluid manipulator 3 in the cavity 14 measured from the top opening 15, during the time t, wherein X represents the total distance of travel and t represents the total time from the moment in which the fluid manipulator enters the cavity 14 until it leaves the cavity 14 and during which time a washing step W and a drying step D take place. According to one example, the total distance X is 150 mm and the total time t is 6 seconds. Line 55 represents the operative status of the wash element 18 and in particular the time when the first fluid pump is on (above line 58) or off (in correspondence to line 58), respectively. It can be seen therefore that the first fluid pump is turned on when the fluid manipulator starts to enter the cavity 14 and remains on during the washing step W, during which the fluid manipulator is gradually passed through the washing zone 33. Line 56 represents the rotational status of the fluid manipulator 3. In particular, the fluid manipulator starts to rotate at a first speed when it reaches the washing zone 33 and continues to rotate at this speed during the washing step W while the fluid manipulator is passed through the washing zone 33 such as to expose all sides of the fluid manipulator to the washing fluid. Once the washing step W is completed, the first fluid pump is turned off and the speed of rotation of the fluid manipulator is increased to a second speed, during the drying step D, in order to remove traces of wash fluid from the fluid manipulator 3 by centrifugation. Line 57 represents the operative status of the wash element 18 acting as drying element, and in particular the time when the second fluid pump is on (above line 58) or off (in correspondence to line 58) respectively. It can be seen that the drying element starts to operate, i.e., the second fluid pump is on only after the washing step W is completed and the first fluid pump is turned off. Thus, the effect of centrifugation of the fluid manipulator 3 is combined with the effect of the drying element during the drying step D in order to achieve faster drying of the fluid manipulator 3. The second fluid pump remains on while the fluid manipulator is passed through the drying zone 53 out of the cavity 14. Once the drying step D is completed the rotation of the fluid manipulator 3 is interrupted (in correspondence to line 58) and the second fluid pump is also turned off.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A wash station for washing one or more reusable fluid manipulators of an automated system for the automated manipulation of fluids, the wash station comprising:
    a cavity for inserting said one or more fluid manipulators, said cavity having one or more washing zones, each of which being sized to receive at least a portion of at least one fluid manipulator;
    each washing zone being coupled to at least one wash element comprising at least one nozzle for connection to a first fluid pump for pumping washing fluid through said nozzle to generate a first fluid jet and at least one deflector surface positioned to deflect said first fluid jet in order to generate a second fluid jet, said deflector surface being shaped such that said second fluid jet is broader than the first fluid jet so as to wash an outside surface of said at least one fluid manipulator residing in said washing zone.

2. The wash station according to claim 1, wherein the at least one wash element is connected to a second fluid pump for pumping drying fluid through said nozzle to generate a fluid jet of drying fluid towards said wash zone.

3. The wash station according to claim 1, wherein said cavity comprises one or more drying zones, each of which being sized to receive at least a portion of at least one fluid manipulator, each drying zone being coupled to at least one drying element comprising at least one nozzle for connection to a second fluid pump for pumping drying fluid through said nozzle to generate a fluid jet of drying fluid towards said drying zone.

4. The wash station according to claim 1 further comprising a plurality of wash elements and/or drying elements specifically adapted to various fluid manipulators.

5. The wash station according to claim 1, wherein said at least one nozzle is integrally formed with said deflector surface.

6. The wash station according to claim 1, wherein said deflector surface is formed by a concave recess, a concave triangular hollow, a convex cap, or a rounded tip.

7. The wash station according to claim 1, wherein said wash element is removably fixed to a mount, wherein said mount is a casing forming said cavity.

8. The wash station according to claim 3, wherein said drying element is removably fixed to a mount, wherein said mount is a casing forming said cavity.

9. An automated system for the automated manipulation of fluids, comprising:
    one or more reusable fluid manipulators for manipulating fluids;
    one or more wash stations for washing said one or more fluid manipulators, the wash stations comprising,
    a cavity for inserting said one or more fluid manipulators, said cavity having one or more washing zones, each of which being sized to receive at least a portion of at least one fluid manipulator, and
    each washing zone being coupled to at least one wash element comprising at least one nozzle for connection to a first fluid pump for pumping washing fluid through said nozzle to generate a first fluid jet and at least one deflector surface positioned to deflect said first fluid jet in order to generate a second fluid jet, said deflector surface being shaped such that said second fluid jet is broader than the first fluid jet so as to wash an outside surface of said at least one fluid manipulator residing in said washing zone;

a moving mechanism for moving said one or more fluid manipulators relative to said one or more wash stations and relative to said cavity, and a first fluid pump for generating said first fluid jet for washing the outside surface of said fluid manipulator.

10. The automated system according to claim 9 further comprising a second fluid pump for generating a fluid jet of drying fluid for drying the outside surface of said fluid manipulator.

\* \* \* \* \*